US010405937B2

(12) United States Patent
Black et al.

(10) Patent No.: US 10,405,937 B2
(45) Date of Patent: Sep. 10, 2019

(54) DRILL COVER AND CHUCK MECHANISM

(71) Applicant: ARBUTUS MEDICAL INC., Vancouver (CA)

(72) Inventors: Marianne Black, Markham (CA); Michael Cancilla, Vancouver (CA); Lawrence Buchan, Port Moody (CA); Elise Huisman, Vancouver (CA); Jeremy Kooyman, Calgary (CA)

(73) Assignee: Arbutus Medical Inc., Vancouver (CA)

( * ) Notice: Subject to any disclaimer, the term of this patent is extended or adjusted under 35 U.S.C. 154(b) by 386 days.

(21) Appl. No.: 15/302,274

(22) PCT Filed: Apr. 9, 2015

(86) PCT No.: PCT/CA2015/050290
§ 371 (c)(1),
(2) Date: Oct. 6, 2016

(87) PCT Pub. No.: WO2015/154188
PCT Pub. Date: Oct. 15, 2015

(65) Prior Publication Data
US 2017/0027658 A1    Feb. 2, 2017

Related U.S. Application Data

(60) Provisional application No. 61/977,461, filed on Apr. 9, 2014.

(51) Int. Cl.
*A61B 46/10* (2016.01)
*A61B 50/30* (2016.01)
(Continued)

(52) U.S. Cl.
CPC .............. *A61B 46/10* (2016.02); *A61B 17/14* (2013.01); *A61B 17/144* (2016.11);
(Continued)

(58) Field of Classification Search
CPC ...... A61B 46/10; A61B 50/30; A61B 17/1622
See application file for complete search history.

(56) References Cited

U.S. PATENT DOCUMENTS 1,272,466 A    7/1918   Larson
1,691,823 A    11/1928  Ogilvie
(Continued)

FOREIGN PATENT DOCUMENTS

DE          422955 C     12/1925
DE       10125186 A1     12/2002
(Continued)

OTHER PUBLICATIONS http://curecaribe.blogspot.ca/2010/02/cure-drill-system.html, Feb. 2010.

*Primary Examiner* — Andrew Yang
(74) *Attorney, Agent, or Firm* — Oyen Wiggs Green & Mutala LLP

(57) ABSTRACT

A cover for a rotary tool allows a non-sterile rotary tool to be used in a sterile field. The cover comprises a flexible enclosure of a sterilizable material and a rotary pass through extending through a wall of the flexible enclosure. A rotary tool within the flexible enclosure is coupled to drive an inner rotatable member on the rotary pass through. The cover prevents the tool (which may not be sterile) from coming into direct contact with anything in a sterile field.

29 Claims, 13 Drawing Sheets

(51) Int. Cl.
*A61B 17/16* (2006.01)
*A61B 17/14* (2006.01)

(52) U.S. Cl.
CPC ...... *A61B 17/1622* (2013.01); *A61B 17/1633* (2013.01); *A61B 50/30* (2016.02)

(56) References Cited

U.S. PATENT DOCUMENTS

| | | |
|---|---|---|
| 6,673,078 B1 | 1/2004 | Muncie |
| 6,716,215 B1 | 4/2004 | David et al. |
| 7,886,743 B2 | 2/2011 | Cooper et al. |
| 2009/0194446 A1 | 8/2009 | Miller et al. |
| 2010/0170519 A1 | 7/2010 | Romo et al. |

FOREIGN PATENT DOCUMENTS

| | | | |
|---|---|---|---|
| GB | 296382 | A | 8/1928 |
| JP | 4369556 | B2 | 11/2009 |
| JP | 4570294 | B2 | 10/2010 |

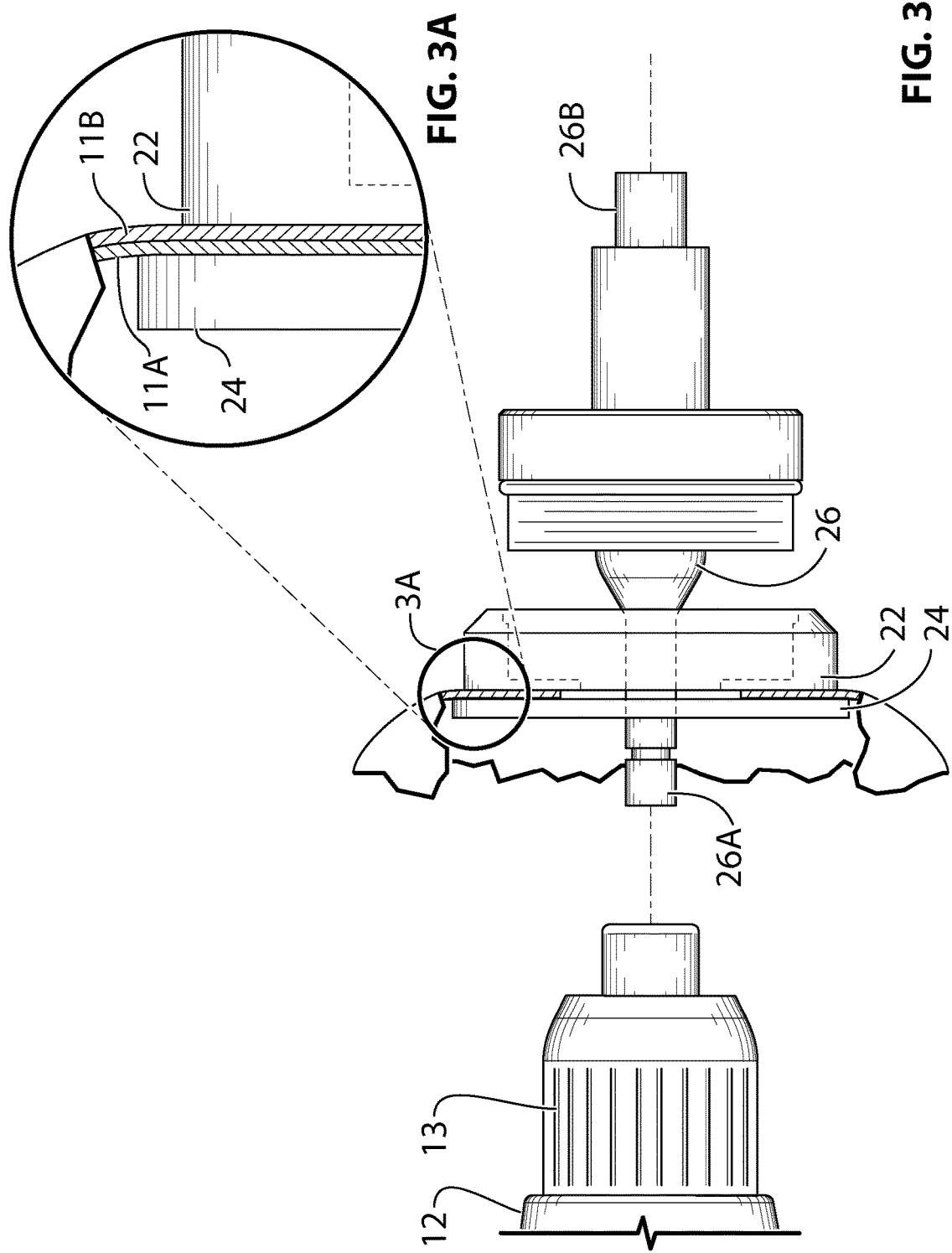

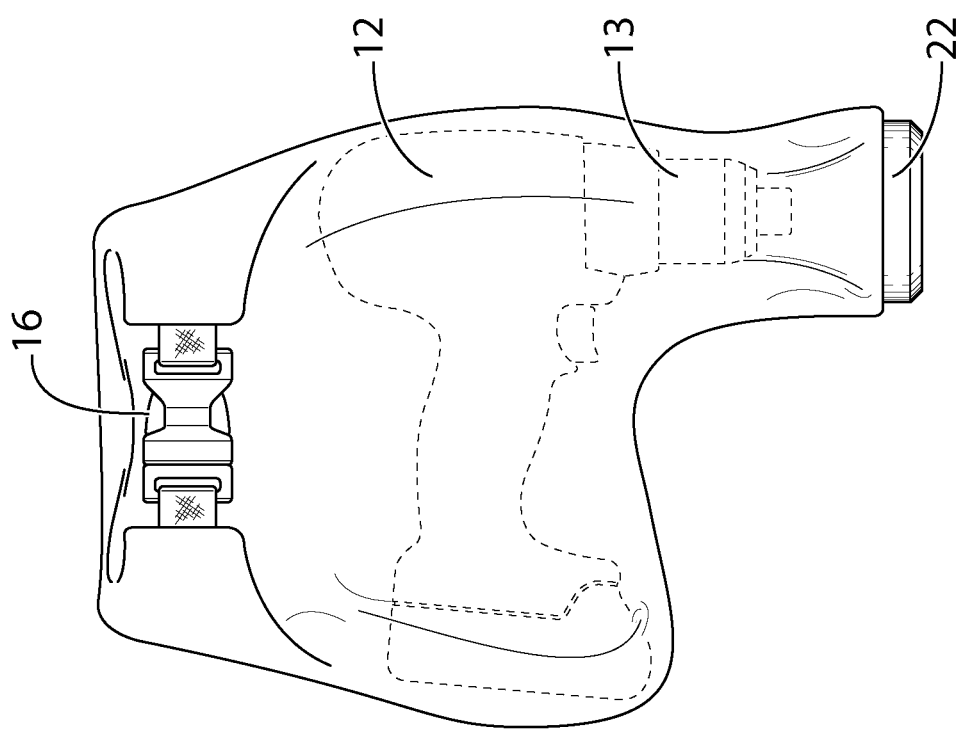

DRILL COVER AND CHUCK MECHANISM

CROSS-REFERENCE TO RELATED APPLICATIONS

This application claims priority from U.S. application No. 61/977,461 filed Apr. 9, 2014. For purposes of the United States, this application claims the benefit under 35 U.S.C. § 119 of U.S. application No. 61/977,461 filed Apr. 9, 2014 and entitled DRILL COVER AND CHUCK MECHANISM which is hereby incorporated herein by reference for all purposes.

FIELD

This invention relates to the field of rotary tools for use in surgery. An example of a rotary tool is a drill.

BACKGROUND

Drills are used in various surgical procedures. For example, a drill may be used by an orthopedic surgeon to drill a hole in bone to receive a screw or wire. Since surgery must be performed with sterile equipment, surgical drills are designed to survive sterilization procedures. Such surgical drills can be exceedingly expensive. Specialized surgical drills can be so expensive that they are unaffordable in some communities.

Battery powered portable drills for use by tradespeople and homeowners are commonly available and are much less expensive than surgical drills. However, commercially available power drills cannot be effectively sterilized and are therefore not usable for surgical purposes.

There is a need for more cost effective ways to provide tools for use in surgery and other environments that require sterilization.

SUMMARY

This invention provides rotary tools suitable for use in sterile environments (e.g. in surgery), covers that may be applied to rotary tools to maintain sterility of a sterile field, and methods for providing a rotary tool for use in a sterile field.

An example aspect of the invention provides a cover for a rotary tool. The cover comprises a flexible enclosure having an inside and an outside and a rotary pass through sealed to the flexible enclosure. The rotary pass through comprises an inside rotatable member on the inside of the enclosure coupled to rotate an outside rotatable member on the outside of the enclosure. The inside rotatable member is configured to engage the rotary tool inside the flexible enclosure. The outside rotatable member is configured to engage a tool (e.g. a drill bit, saw, wire, reamer or the like). The flexible enclosure has an opening dimensioned to allow the rotary tool to be put into or removed from the enclosure and a closure arranged to close the opening.

Another example aspect of the invention comprises a method for providing a rotary tool for use in a sterile environment. The method comprises: placing a battery-powered rotary tool into a flexible enclosure through an opening in the enclosure; coupling the rotary tool to drive an inner end of a rotary pass through that extends through a wall of the flexible enclosure; and closing the opening. The steps of coupling the rotary tool to drive the rotary pass through and closing the opening may be performed in either order.

According to some aspects of the invention a cover comprises a feed through configured to pass reciprocating and/or rotary motion from the inside of the cover to the outside of the cover. In an example of such an aspect a cover for a reciprocating tool comprises a flexible enclosure having an inside and an outside and a reciprocating pass through sealed to the flexible enclosure. The reciprocating pass through comprises an inside reciprocatable member on the inside of the enclosure coupled to reciprocate an outside reciprocatable member on the outside of the enclosure. The inside reciprocatable member is configured to engage the reciprocating tool inside the flexible enclosure. The outside reciprocatable member is configured to engage a tool. The flexible enclosure has an opening dimensioned to allow the reciprocating tool (e.g. a battery-powered reciprocating saw) to be put into or removed from the enclosure and a closure arranged to close the opening.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

FIG. 1 is a partially cut-away side elevation view showing a surgical drill made up of a drill and a sterile cover which includes a rotary feed-through.

FIG. 3 is a cut away side elevation view of a rotary feed-through with a rotary tool on a non-sterile side of the feed-through. FIG. 3A is a detailed view illustrating one way to seal a rotary feed through to a flexible enclosure. FIG. 3B is a perspective view from an inside of the enclosure showing a retaining ring for a rotary feed-through.

FIGS. 5A through 5F illustrate steps in a method for loading a tool into a sterile enclosure and preparing the tool for use in surgery.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

One aspect of the invention provides a sterilizable cover which may be used to allow a non-surgical rotary tool (i.e. a rotary tool that is not designed to survive hospital sterilization procedures and therefore cannot be considered to be sterile) to be used in a setting which requires sterility. The tool may, for example, be a power drill or power screwdriver. The cover includes a flexible enclosure which has an inside and an outside. A rotary pass-through is sealed to the flexible enclosure. The rotary pass-through may be coupled to a non-sterile rotary tool on the inside of the cover and may pass rotation to a chuck or other rotatable member on the outside of the enclosure. The flexible enclosure has an opening which is dimensioned to allow the rotary tool to be put into or removed from the enclosure and a closure arranged to keep the opening closed during surgery.

Figure 1:
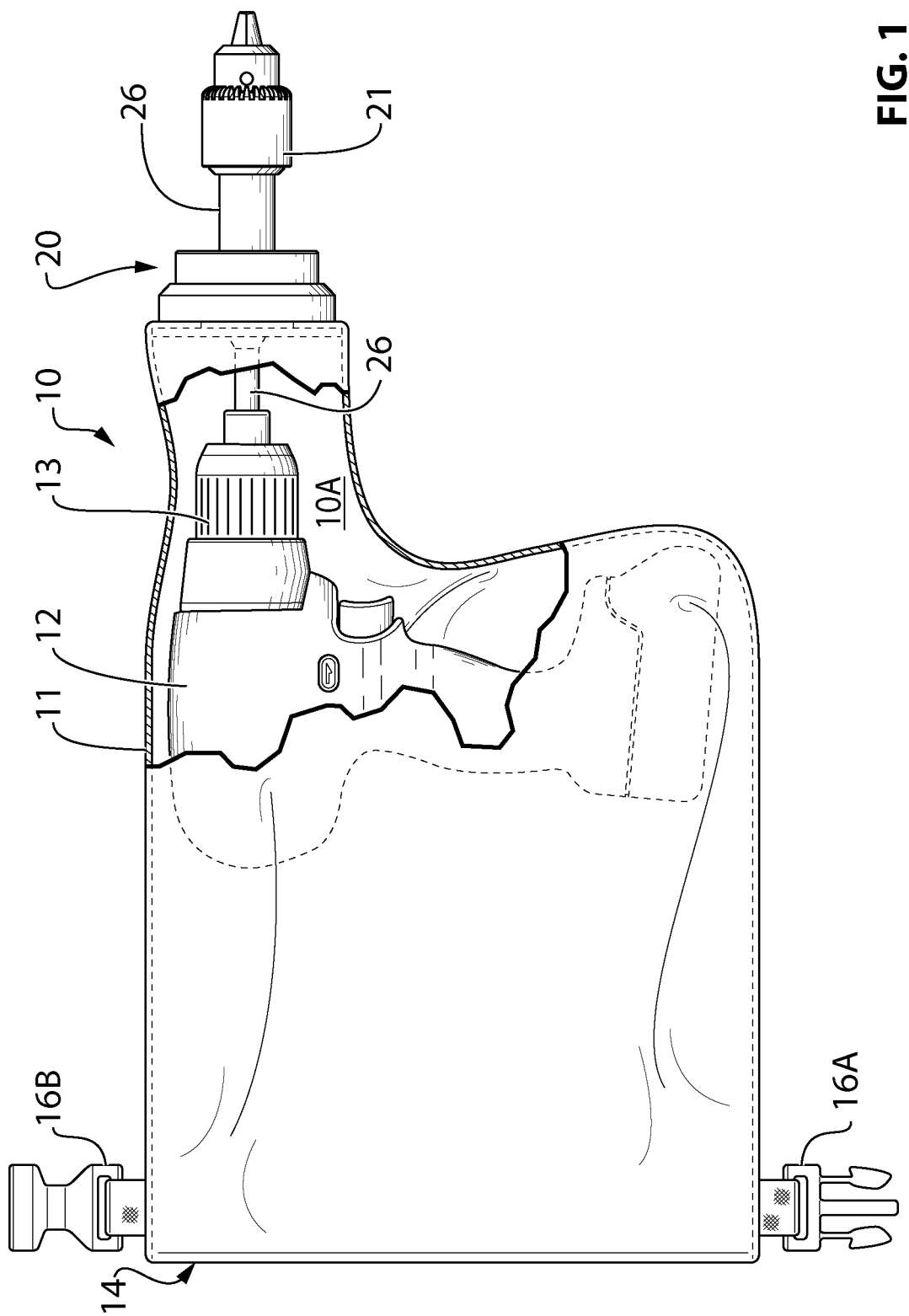
Figure 2:
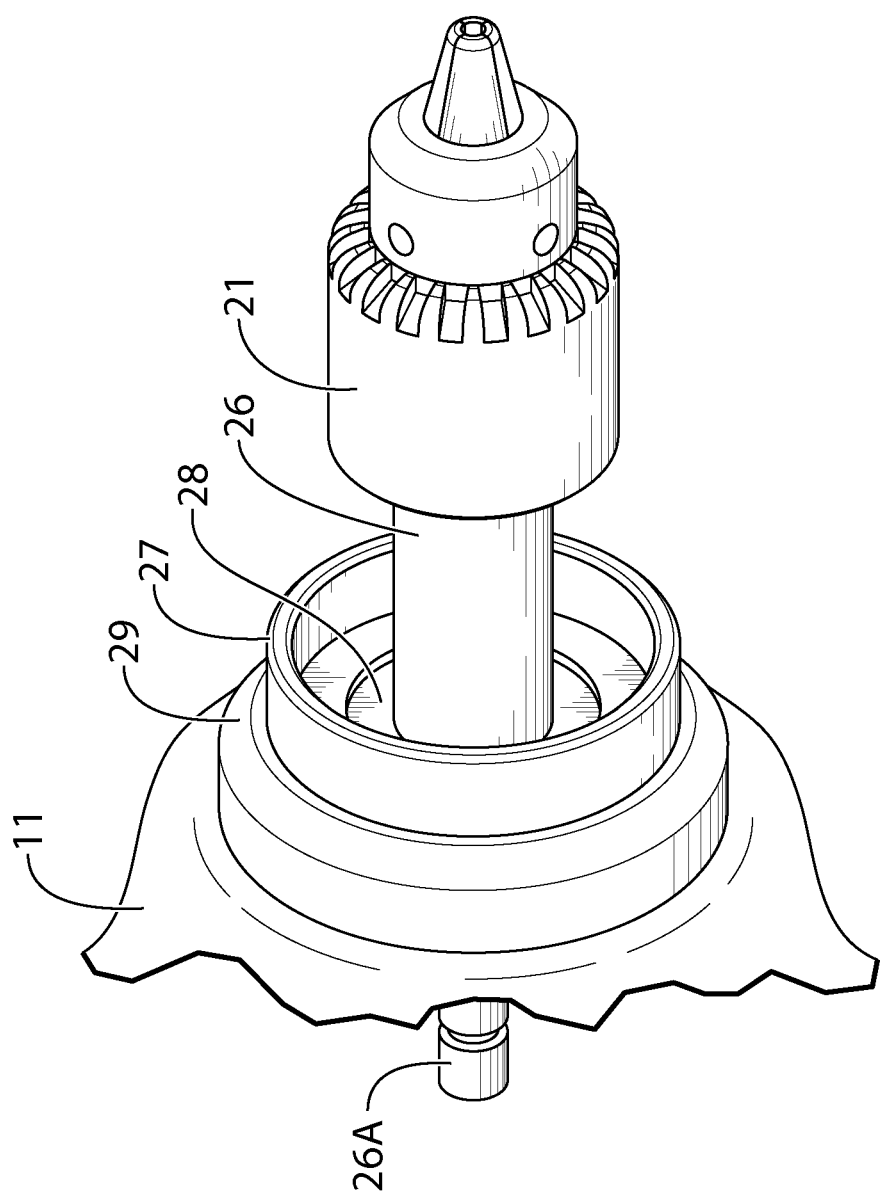
FIG. 2 is close up view of a rotary feed-though that includes an external chuck mechanism.

FIG. 1 shows a cover 10 according to an example embodiment of the invention. A rotary tool 12, in this case a power screwdriver, is located inside cover 10. Cover 10 provides a barrier between tool 12 and a sterile field. Cover 10 includes an enclosure 11 in the form of a flexible bag. An opening 14 is dimensioned to allow a tool 12 (e.g. a power screwdriver, drill or another rotary tool) to be put into or removed from the inside of cover 10.

Bag 11 may be sewn or otherwise shaped to conform generally with the shape of tool 12. For example, where tool 12 is a drill or power screwdriver having a handle extending generally at right angles to a body then the bag may have a generally L-shaped configuration in which the body of the tool fits into one arm of the L-shaped bag and the tool handle fits into the other arm of the L-shaped bag. In some embodiments the arm of the L-shaped bag that receives the body of tool 12 is generally cylindrical. In some embodiments an arm of a bag that receives the body of tool 12 extends generally perpendicular to opening 14 such that when cover 12 is held with opening 14 uppermost and open the arm of the bag that receives the body of tool 12 extends generally vertically.

In an alternative embodiment the bag may be less shaped to fit tool 12. For example bag 11 may comprise a rectangular bag. Bag 11 may be sized to receive tool 12. For example, bag 11 may be approximately 30 cm×25 cm in some embodiments.

A closure 16 is provided for opening 14. In the illustrated embodiment, closure 16 comprises a buckle comprising parts 16A and 16B. In an example embodiment, buckle parts 16A, 16B are made of nylon 6,6 and can be safely heated to temperatures expected in autoclave sterilization. Nylon 6,6 can typically be heated to temperatures of about 390 F. (about 200 C.) without damage. Other embodiments have other styles of closures for opening 14 such as suitable zippers, adhesive flaps, snap fasteners, hooks, or the like.

Tool 12 may be a standard off-the shelf power tool of the type that may be used by tradespersons or homeowners. Brand names for such tools include Dewalt™, Milwaukee™, Bosch™, Makita™, Rigid™ and Panasonic™. Such tools 12 are commonly-available worldwide and are very inexpensive in comparison to purpose-made surgical drills.

Tool 12 ideally has the following characteristics:
speed matching conventional surgical drills (e.g. 1000-1300 rpm),
torque matching conventional surgical drills (e.g. 6-20 Nm),
light weight (e.g. less than 1 kg is best),
battery operated, and
robust (i.e. not prone to requiring complex maintenance on a regular basis; can be operated reliably for long periods without special maintenance).

Bag 11 may be made of any of a wide variety of materials or combinations of materials. Materials for bag 11 should have surfaces suitable for use in sterile environments and should be able to withstand sterilization procedures. Some desirable characteristics for the material of bag 11 are: cleanable; non-linting; resistant to penetration by bacteria and fluids; anti-static; and durable through multiple sterilization cycles. An example of a suitable material for bag 11 is Maxima EX™ available from Burlington Barrier of Seattle USA.

In other example embodiments the material of bag 11 comprises a reinforced nylon material. Nylon can withstand autoclaving. Other materials that may be suitable for cover 10 are thermoplastic materials. Such materials include materials such as polyester, nylon (polyamide), bondable polyurethane, neoprenes, polypropylenes and the like. Some specific example fabrics that may be used for material 11 include:
Seattle Fabrics 330 Denier Supplex Cordura Urethane Coated Nylon;
Seattle Fabrics 1.9 oz Silicone Coated Nylon (White);
Seattle Fabrics 1.9 oz Urethane Coated Nylon (White);
Seattle Fabrics Sur Last; and,
Seattle Fabrics WeatherMax.

In some embodiments, the material of bag 11 is provided in two layers, an inner layer 11A and an outer layer 11B. These two layers provide a factor of safety in case the outer layer becomes torn or is otherwise compromised. In some embodiments, at least the outer face of inner layer 11A has a colour that contrasts with the outer face of outer layer 11B. This contrast in colour makes it easier to detect visually damage such as cuts, openings or highly worn areas in outer layer 11B.

The material of bag 11 may be formed to make bag 11 by any suitable fastening method including stitching, ultrasonic welding, heat bonding, adhesive bonding, or the like. In an example embodiment, the material is stitched together to provide bag 11 using a suitable thread (e.g. a polyester cotton thread). Where bag 11 has seams at which material is joined together then the seams may optionally be covered with a seam sealing tape. The seam sealing tape may, for example, comprise an EPTFE material. An example of a suitable seam sealing tape is GORE-SEAM® Tape available from W. L. Gore & Associates, Inc. of Elkton, Md., USA. Seam sealing tape helps to further prevent any liquid from penetrating through the seams of bag 11.

Cover 10 includes a pass-through mechanism (which may be described as a 'rotary pass-through') indicated generally by 20 that is sealed to bag 11. Pass-through mechanism 20 is sealed around its edges to an opening in bag 11. In some embodiments the attachment between pass-through mechanism 20 and bag 11 is a mechanical attachment designed to permit removal of bag 11 from pass-through mechanism 20 and replacement with a new bag 11 coupled to pass-through mechanism 20. This may be done, for example, when a bag 11 becomes worn out or damaged. In some cases bag 11 may be preemptively replaced after every so many sterilization cycles.

Where bag 11 is shaped to fit a particular type of tool, pass-through mechanism 20 may be located to be adjacent to a moving part of the tool (e.g. a chuck) when the tool is received in bag 11. Covers 10 for different types of tools may have pass-through mechanism 20 at different locations relative to features of bag 11 such as opening 14 or features of shape intended to conform to parts of the tool. For example a pass-through mechanism in a cover intended for a drill or power screwdriver may have a different orientation relative to opening 14 from a pass-through mechanism in a cover intended for a battery-powered circular saw.

Figure 3B:
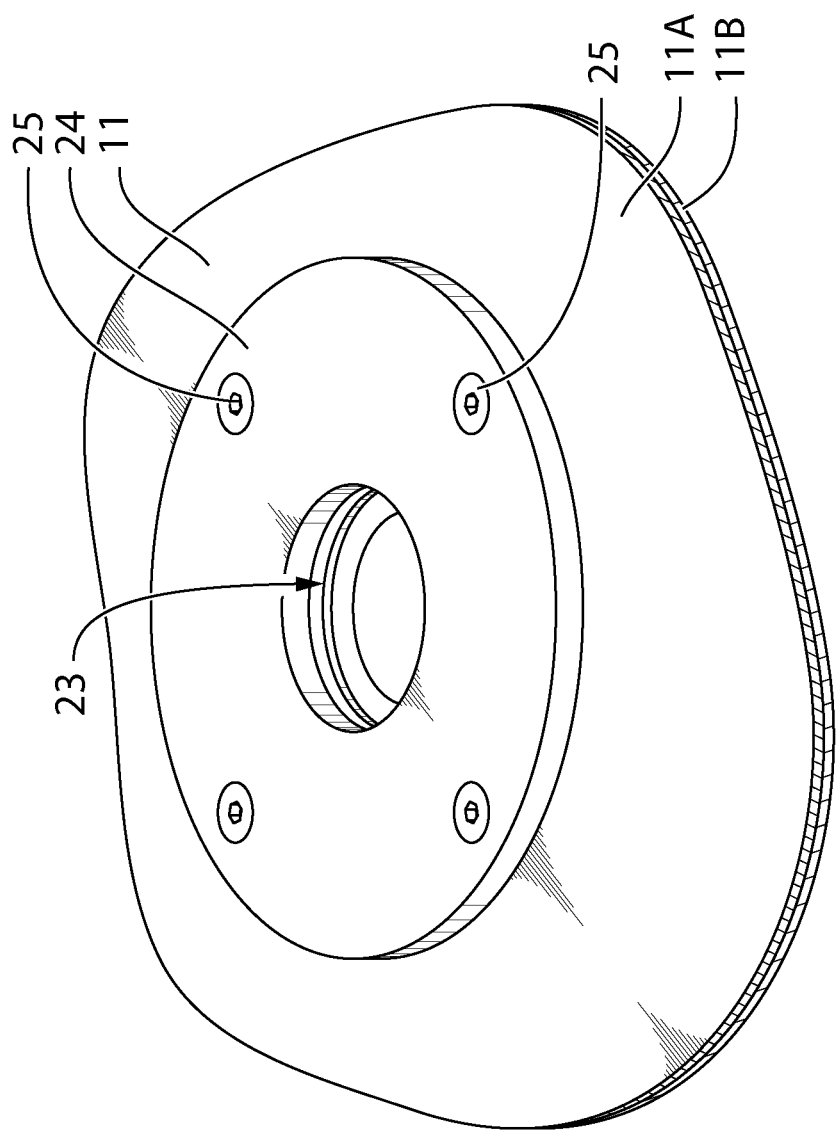

In the illustrated embodiment, pass-through mechanism 20 comprises a baseplate 22 and a backup ring 24. Material 11 is clamped between baseplate 22 and backup ring 24, for example by screws 25 (see FIGS. 3, 3A and 3B). In an example embodiment the material of bag 11 tends to become somewhat adherent to baseplate 22 and backup ring 24 under the force clamping baseplate 22 and backup ring 24 together and the conditions experienced when cover 10 is sterilized in an autoclave. This adherence helps to make bag 11 stay in place better.

A shaft 26 extends from the inside 10A of cover 10 to the outside of cover 10 through openings 23 in baseplate 22 and backup ring 24. An inner end 26A of shaft 26 can be engaged with a chuck 13 of tool 12. An outer end 26B of shaft 26 carries a chuck 21 or other coupling operable to grasp and turn a drill, saw, wire, or other object that requires turning in a sterile field. Chuck 21 may, for example, comprise a three-jaw chuck. In some embodiments chuck 21 is a keyless 3-jaw chuck.

Figure 4:
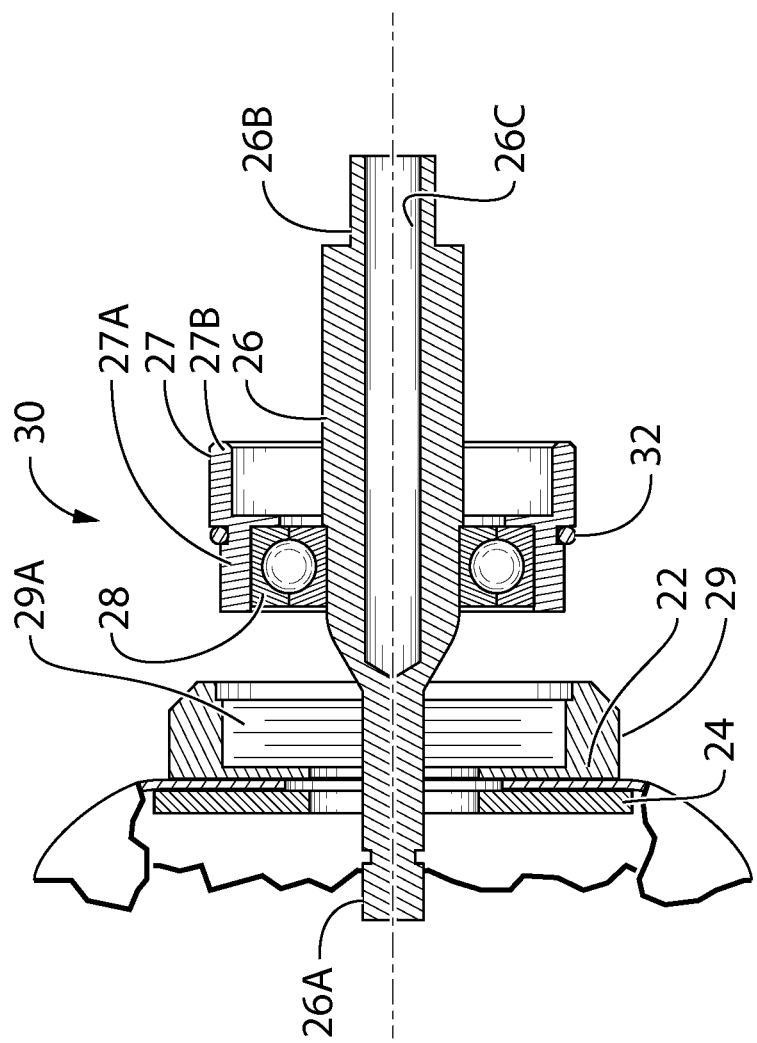
FIG. 4 is a cross-sectional view of a rotary feed-through according to an example embodiment.
Figure 4A:
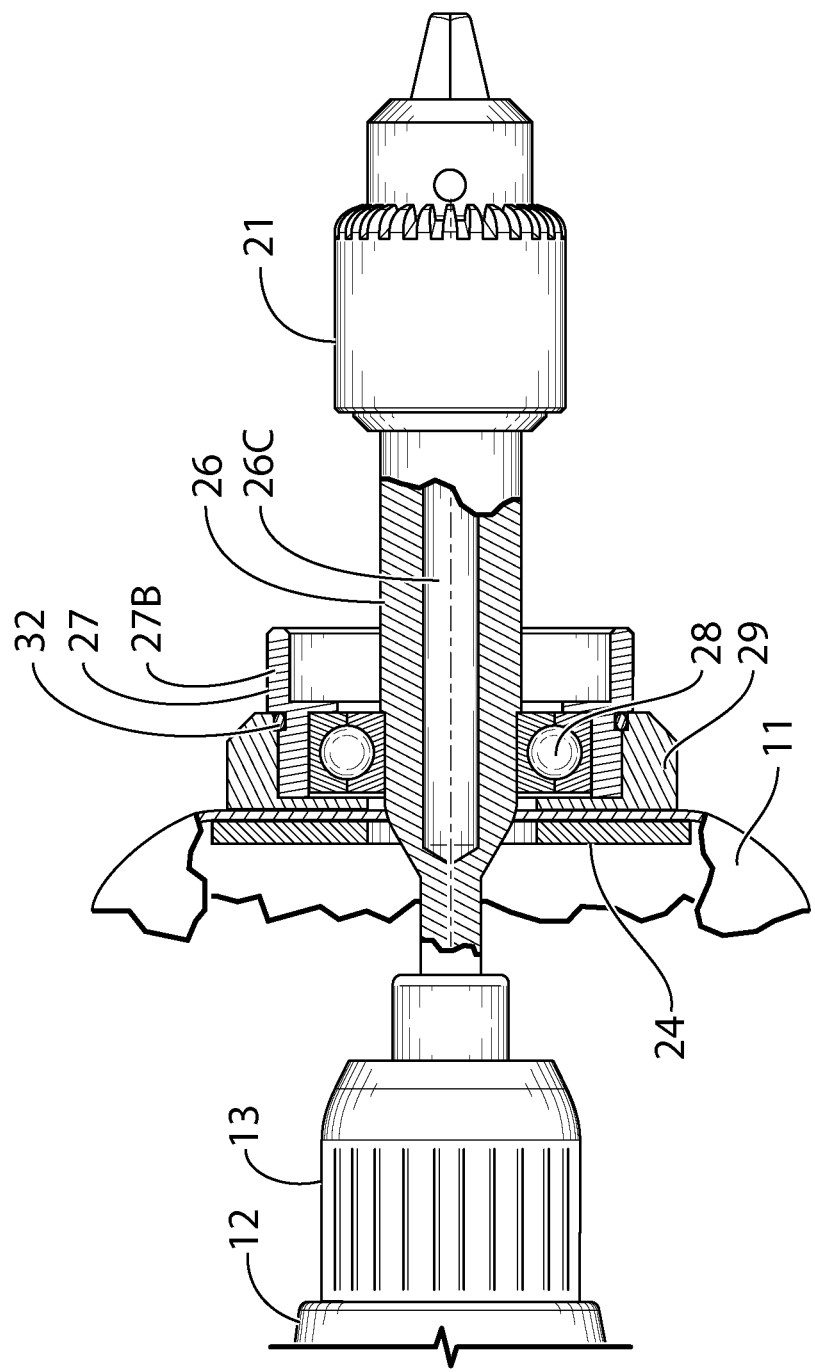
FIG. 4A shows the rotary feed-through of FIG. 4 with a tool coupled to drive the non-sterile end of a shaft and a chuck affixed on a sterile end of the shaft.

Shaft 26 may be supported on baseplate 22 in a wide variety of ways. In the illustrated embodiment (see e.g. FIGS. 4 and 4A), shaft 26 is rotatably supported in a bearing carrier 27 by a bearing 28. It is convenient but not mandatory for bearing carrier 27 to be removably attached to baseplate 22. This construction is advantageous because it allows shaft 26 to be easily engaged with the chuck 13 of tool 12 after tool 12 has been placed in the inside 10A of cover 10.

In the illustrated embodiment, a collar 29 extends from baseplate 22 and a shaft assembly 30 comprising bearing carrier 27, bearing 28 and shaft 26 is adapted to be removably coupled to collar 29. In the illustrated embodiment, bearing carrier 27 is threaded on its outer surface 27A and collar 29 has compatible internal threads 29A. Alternative arrangements such as a bayonet coupling, a twist lock coupling, a "snap-together" connection, or the like may be provided to secure shaft assembly 30 to baseplate 22.

In the illustrated embodiment, a seal 32, such as an O-ring, is provided to ensure that non-sterile material cannot exit from the inside of cover 10 between bearing carrier 27 and collar 29 when bearing carrier 27 is in place. Seal 32 also prevents infiltration of fluids into the coupling between bearing carrier 27 and baseplate 22.

In the illustrated embodiment, an axially-projecting ring 27B provides a surface that a user can hold to screw bearing carrier 27 into or out of collar 29 and/or to steady tool 12.

Bearing 28 may be, for example, any suitable roller or ball bearing or bushing or sleeve bearing which permits free rotation of shaft 26 relative to bearing carrier 27. Bearing 28 should permit shaft 26 to spin freely relative to bearing carrier 28 so that operation of tool 12 does not cause cover 10 to be significantly pulled around shaft 26. Bearing 28 preferably has shields or seals which obstruct the passage of any material through bearing 28 from the inside 10A of cover 10 to the outside of cover 10 or vice versa.

Bearing 28 ideally has a construction that:
provides a long lasting seal that resists the penetration of liquids and solids;
does not require much maintenance;
resists corrosion;
will not shed particles or lubricant outside of cover 10 even if it is subject to failure or wear;
will not be damaged by autoclave sterilization (e.g. at a temperature of 130 C.); and,
has a coefficient of thermal expansion similar to that of bearing carrier 27 and shaft 26 so that bearing 28 does not thermally expand when heated to sterilization temperatures by an amount that is greatly different from expansions of shaft 26 or bearing carrier 27.

A prototype design uses ball bearings with a polyamide seal for bearing 28.

Bearing 28 may optionally be lubricated with a lubricant. If bearing 28 is lubricated then any lubricant used is advantageously non-toxic and can handle the temperatures expected in autoclave sterilization. In one example embodiment, bearing 28 is lubricated with a high temperature non-toxic lubricant such as Cassida Grase RLS 2. Other example embodiments use other lubricants non-harmful to humans such as petroleum jelly, Vaseline™, or Neosporin™.

In other embodiments, bearing 28 is not lubricated. Lubrication of bearing 28 is generally not required since bearing 28 is generally not operated under any significant load and the duration of most surgical drilling operations is fairly short. In some embodiments, bearing 28 is flushed with suitable solvents to remove any lubricant before the bearing is used in cover 10.

Some rotary tools have chucks that are adapted to grip a hexagonal bit. For example, many power screwdrivers include quick-change chucks for engaging screwdriver bits having this configuration. Such chucks are typically operated to engage or detach from a bit by sliding a spring-loaded collar longitudinally In the illustrated embodiment, the inner end of shaft 26 is configured to releasably engage a quick connect chuck such as, for example, a Quick-Hex™ or another quick release hex chuck system. Inner end 26A of shaft 26 may have the same form as such commonly-available screwdriver bits. Inner end 26A may, for example, be hexagonal in cross section. In some embodiments, inner end 26A is hexagonal and has a dimension of ¼ inch (6.35 mm) across flats of the hex and has a circumferential groove compatible with a chuck of a rotary tool such as a drill or power screwdriver 12.

In some embodiments (see e.g. FIG. 4), the outer end 26B of shaft 26 is hollow. The illustrated embodiment provides a blind bore 26C extending to the outer end 26B of shaft 26. Bore 26C serves as a cannulation that can receive the proximal end of a tool or wire. This allows a surgeon to "choke-up" on a wire or other tool during procedures such as those when a bone is being stabilized with wires.

Where cannulation is not needed, a shorter shaft 26 can be beneficial since with a shorter shaft 26, sterile chuck 21 can be located closer to the power screwdriver 12 than would otherwise be possible. A shorter shaft 26 can provide better balance and accuracy as well as lighter weight. In cases such as the illustrated embodiment where shaft 26 is removable from baseplate 22, apparatus according to the invention may provide interchangeable shafts 26. Each shaft 26 is provided as part of a shaft assembly 30 in some embodiments. For example, one shaft 26 may be provided with a bore 26C. Another shaft 26 may be provided without a bore 26C. The second shaft 26 may be shorter and lighter than the first shaft 26.

It is also possible to provide two or more shafts 26 having bores of different depths. For example, another shaft 26 may be longer and have a deeper bore 26C than the second shaft. In some embodiments a shaft 26 has a through bore. Such an embodiment may be used in a case where power tool 12 is cannulated (i.e. has a through-bore). In such embodiments a sterile liner may be provided in the through-bore of tool 12.

The outer end 26B of shaft 26 includes a mechanism for gripping a tool bit, wire, or other object which requires rotation in a sterile field. Any of a side variety of different chucks and grippers may be provided at the outer end 26B of shaft 26. These may include: three-jaw chucks, two-jaw chucks, collets, wire grippers, AO-style chucks, etc. A chuck 21 (or other gripping mechanism) may be mounted to shaft 26 in any suitable way including, for example, by making chuck 21 integral with shaft 26, threading chuck 21 onto shaft 26, pinning chuck 21 in place on shaft 26, engaging chuck 21 on a self-locking taper on shaft 26, or some combination of these.

In the illustrated embodiment, chuck 21 is a three-jaw chuck. Chuck 21 is selected to be amenable to sterilization. In preferred embodiments, chuck 21 is made of stainless steel. Stainless steel can withstand heat and chemical sterilization.

Some embodiments provide two or more interchangeable shaft assemblies 30 in which shafts 26 carry different types of chucks 21. For example, one shaft assembly may include a three jaw chuck 21. Another shaft assembly may include an AO style chuck adapted to receive tools having shanks that are D-shaped in cross section. Another shaft assembly may include a collet chuck.

Some embodiments provide a shaft assembly that includes a wire gripper in place of chuck 21. In some embodiments the wire gripper may include a quick-release lever for selectively gripping or releasing a wire. Actuation of the lever may, for example, rotate a cam that selectively clamps the wire against a surface or releases the wire depending on a position of the lever. In an example embodiment the wire gripper comprises a U-shaped channel sized to pass a wire and a lever-operated cam that has a locked position wherein the cam compresses the wire into the channel and an unlocked position wherein the wire can be slid longitudinally along the channel.

The entire cover 10, including rotary pass-through 20, is sterilizable, preferably by autoclaving. In some embodiments, the entire cover 10 is autoclavable at temperatures of at least 120° C. This allows cover 10 to be effectively sterilized prior to use. In some embodiments, cover 10 is tested to ensure that it can prevent contamination of the outside of cover 10 by non-sterile materials inside cover 10. The testing may, for example, be performed as specified in ASTM F1670—Standard Test Method for Resistance of Materials Used in Protective Clothing to Protection by Synthetic Blood.

Figure 5A:
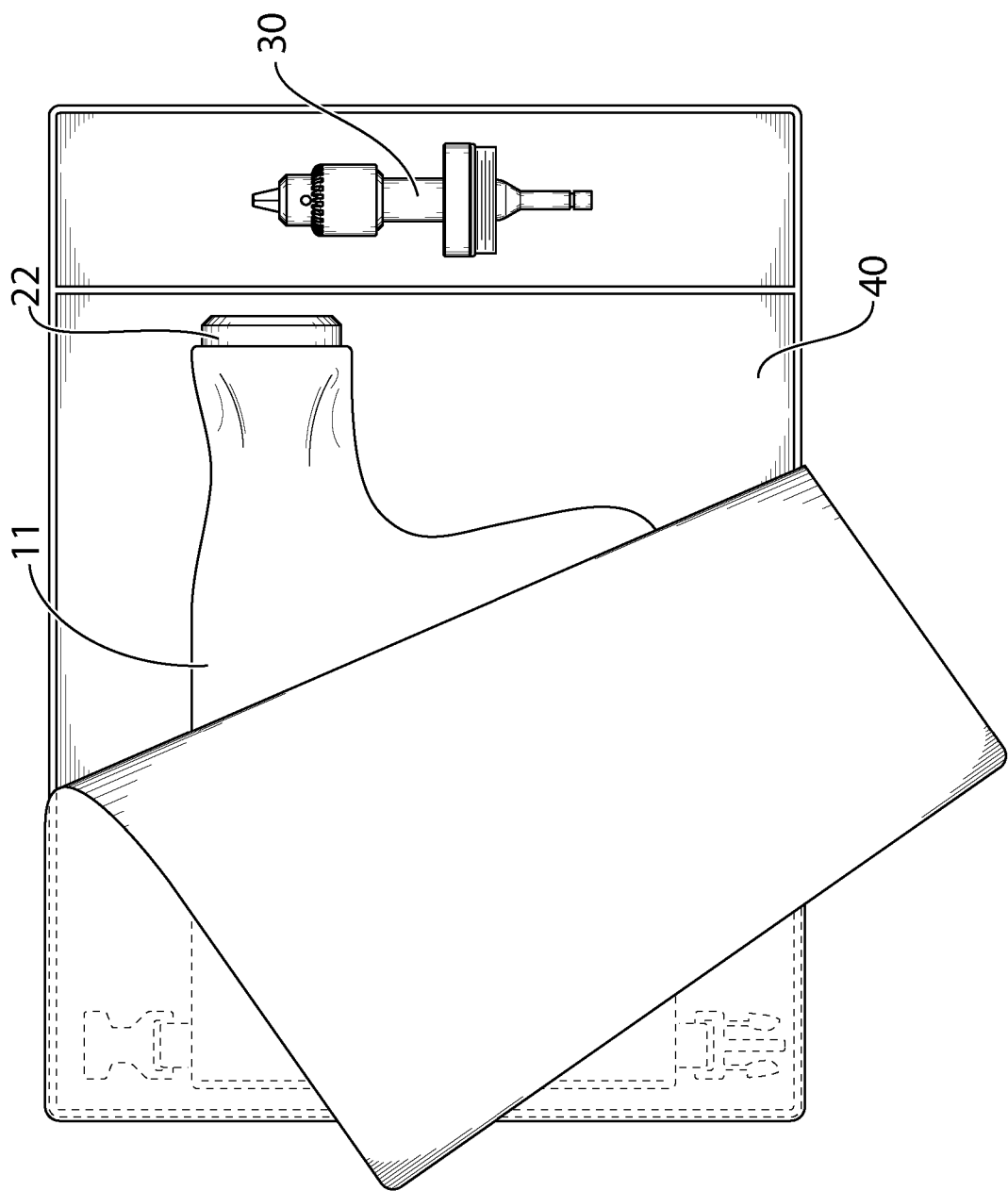
Figure 5B:
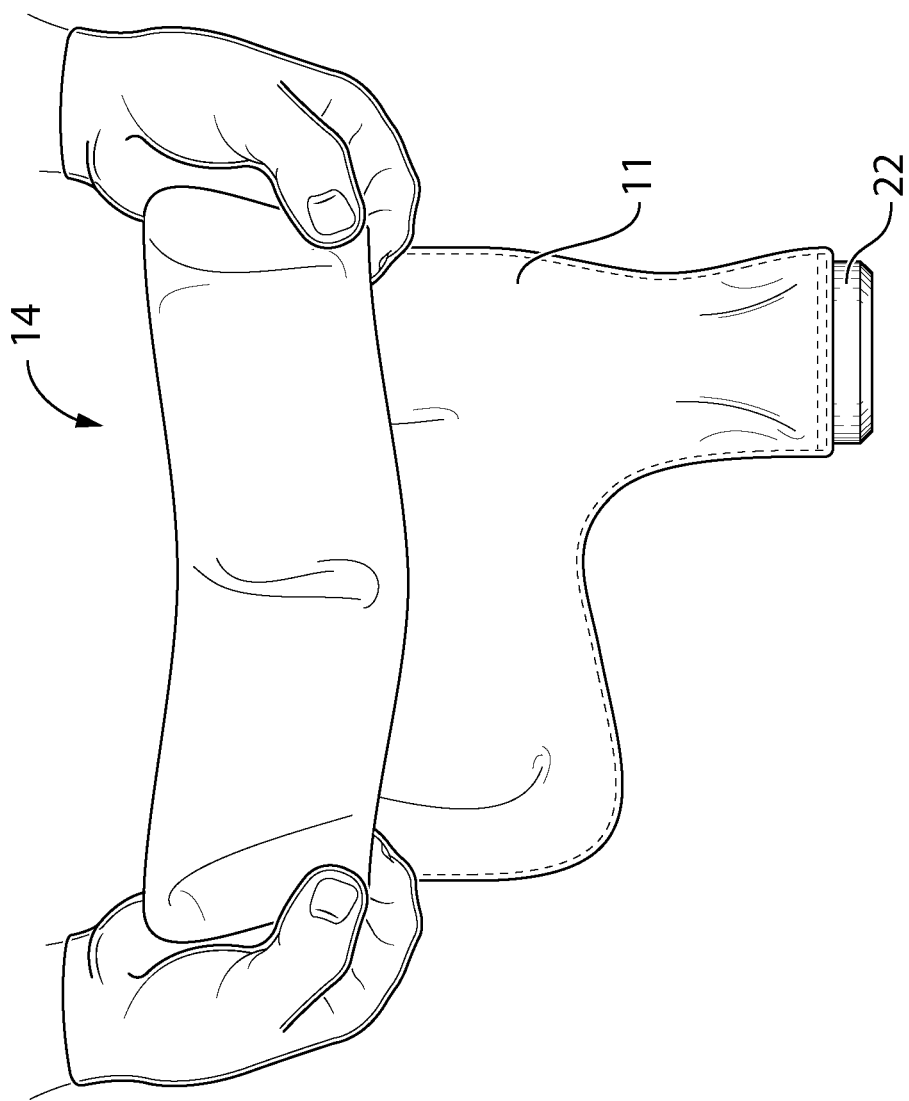
Figure 5C:
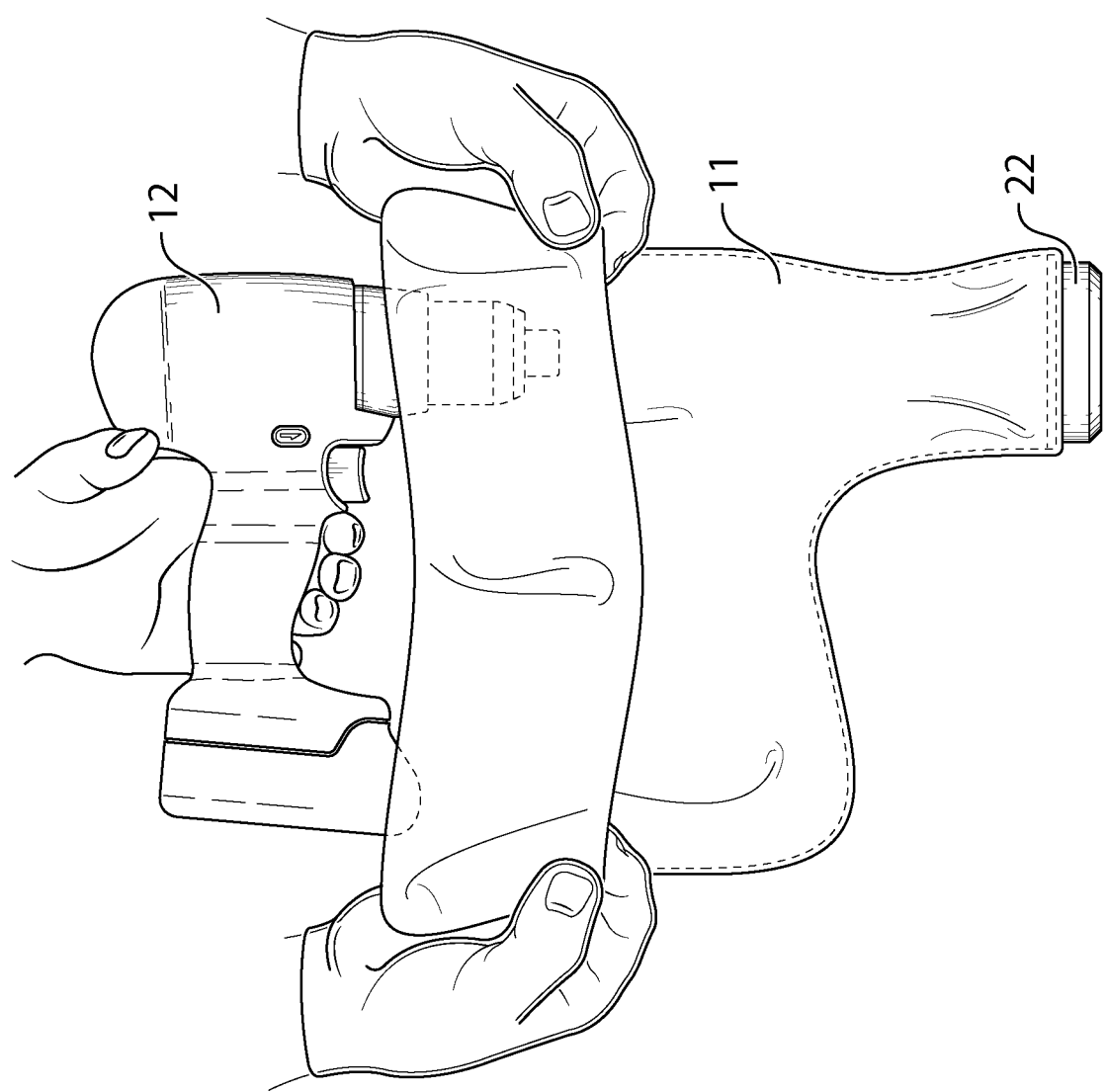
Figure 5D:
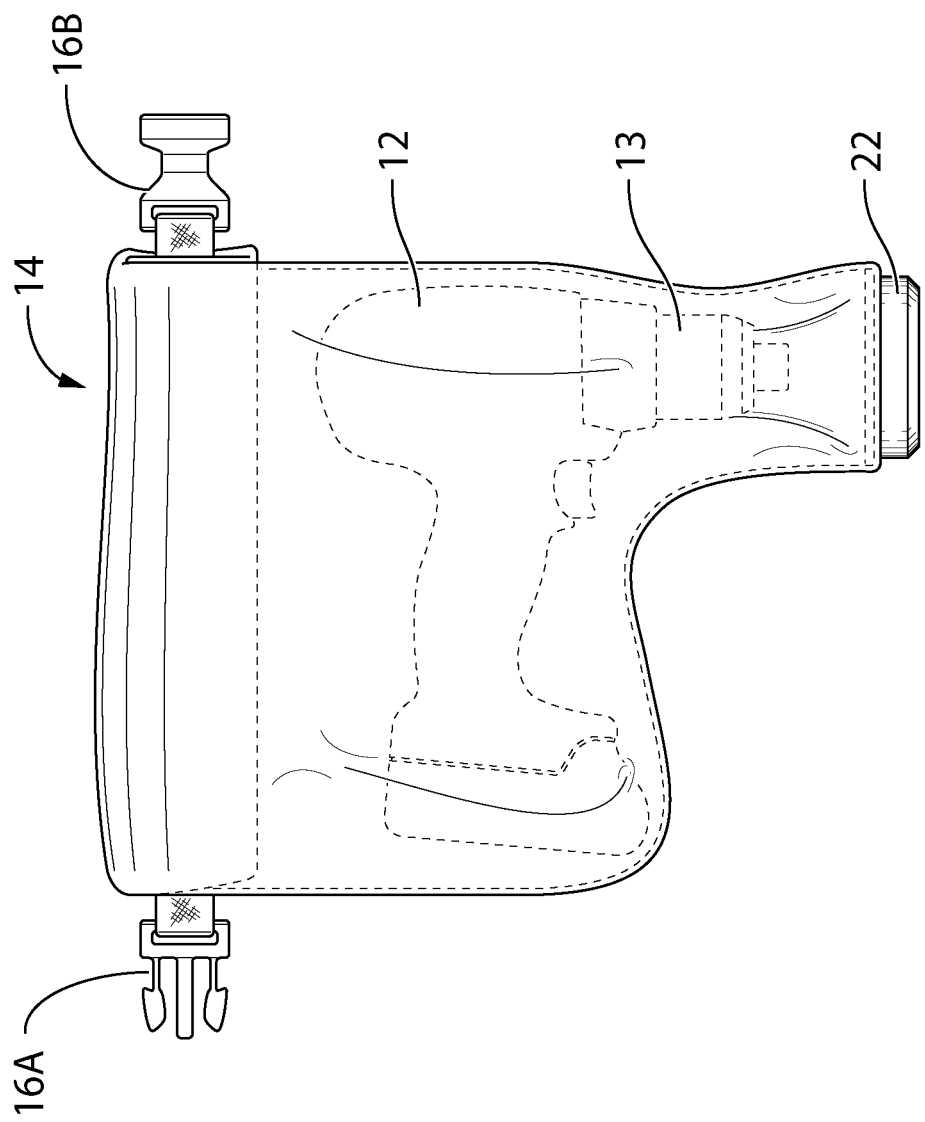
Figure 5F:
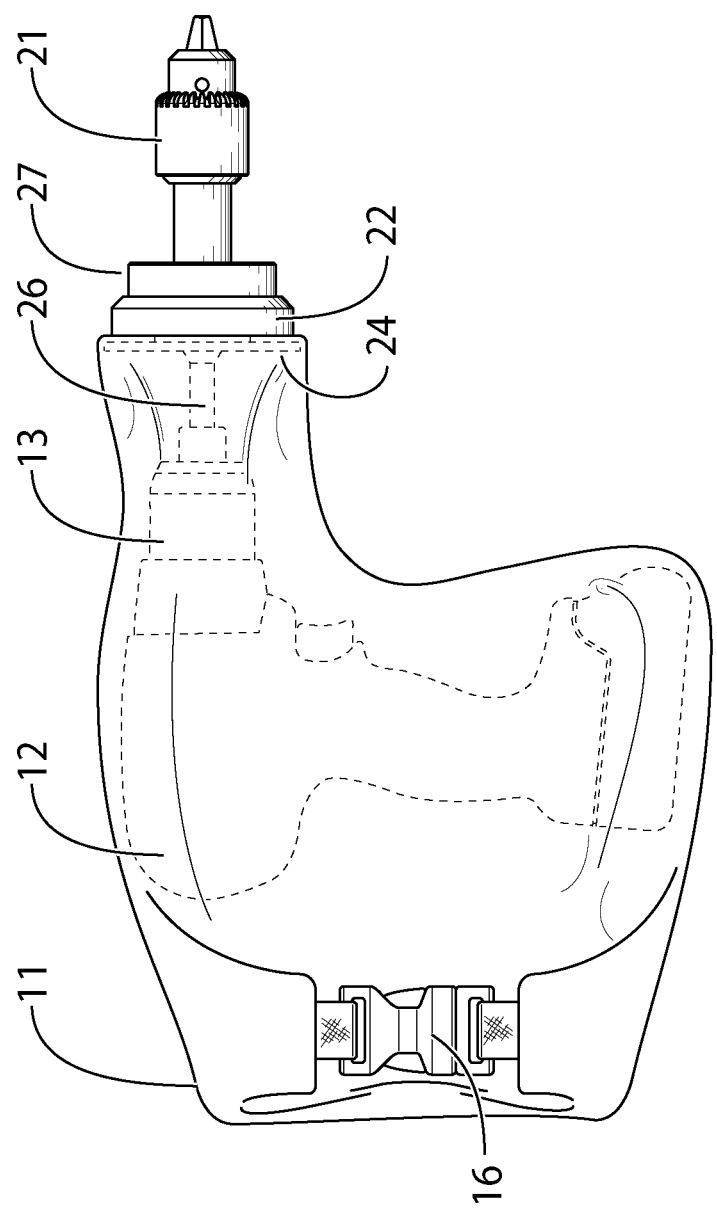

FIGS. 5A to 5F illustrate a sequence of steps in an example method of use of a cover 10 as described herein. Cover 10 is initially sterile. In some cases cover 10 is supplied contained within a sterile package 40 (FIG. 5A). Shaft assembly 30 is removed from cover 10. In a first step a sterile surgeon rolls the edge of cover 10 surrounding opening 14 over his or her fingers and holds open opening 14 as shown in FIG. 5B. A rotary battery-powered power tool 12 (e.g. a power screwdriver or drill) is prepared and placed into cover 10 by an assistant (FIG. 5C). It is not necessary for tool 12 to be sterile.

With tool 12 inside cover 10, the edge of opening 14 is unrolled (FIG. 5D) and then opening 14 is closed by closure 16. In the illustrated embodiment this is done by folding the edge of cover 14 adjacent to opening 14 over upon itself a few times (e.g. 3 times) and then fastening buckle parts 16A and 16B to one another (FIG. 5E).

Shaft 26 may then be coupled to tool 12. This may be done by poking end 26A of shaft 26 through the opening 23 in baseplate 22 to engage the chuck of tool 12 which is now inside cover 10. Shaft assembly 30 may then be secured to baseplate 22 (e.g. by screwing bearing carrier 28 into collar 29).

Once a power screwdriver or other rotary tool has been installed inside cover 10 and coupled to drive shaft 26 (FIG. 5F), a surgeon or other personnel can operate tool 12 by manipulating its controls through the material of bag 11.

Various optional features may be provided. For example, in some embodiments, some or all of cover 10 is made of a transparent material so that a user can more easily see the locations of the controls of rotary tool 12 through cover 10 and/or view displays on the tool 12 such as a battery level indicator or the like. In other embodiments, markings are provided on the outside of cover 10 to indicate the expected locations of certain controls of a power tool located inside cover 10.

In some embodiments cover 10 is configured to work with common surgical drills. The adaptation may comprise, providing a shank compatible with an AO style chuck on the inner end of shaft 26. Although special purpose surgical drills can be sterilized, sterilization takes time. The use of covers 10 may facilitate the use of a surgical drill in high throughput situations without requiring the surgical drill to be re-sterilized between operations.

Optionally bag 11 is made with a folded over flap of material on either side of opening 14. A sterile user may place his or her hands under these flaps to hold opening 14 open to receive a tool 12 (as an alternative to rolling over the edge of opening 14 as described above). In some embodiments the flaps may be folded into the inside of cover 10 before opening 14 is closed.

In some embodiments cover 10 may comprise one or more disposable parts. For example, bag 11 may be disposable. A disposable bag 11 may be made of nitrile rubber (as in surgical gloves), neoprene, latex, or polyethylene (as in a plastic bag.) Pass-through assembly 20 may be re-used with different disposable bags. In such embodiments, Pass-through assembly 20 may include a mechanism which allows for quick changeover of the bags. For example, backup ring 24 may have a 'snap on' coupling to baseplate 22 or may be magnetically coupled to baseplate 22 such that a disposable bag may be trapped between them.

It is not mandatory that all parts of bag 11 be flexible. In alternative embodiments, some parts of bag 11 may be provided by a stiffer sterilizable material.

In some embodiments, rotary pass through 20 comprises one or more members that project into the interior 10A of cover 10 to bear against tool 12. Such members may help to keep the axis of shaft 26 fixed relative to the axis of chuck 13 of tool 12 in cases where there is play in the coupling between shaft 26 and chuck 13. Such members may, for example, resiliently engage sides of the body of tool 12.

In some alternative embodiments a cover essentially as described herein is provided for a reciprocating tool such as a battery-powered reciprocating saw. A difference between such alternative embodiments and the embodiments described above is that a rotary pass-through is replaced by a pass through that permits transmits reciprocating movement from inside the cover to outside the cover. The cover may otherwise have any of the constructions encompassed by the description herein.

A reciprocating pass through may comprise, for example, a baseplate that is sealed to a bag 11 as described above and supports a bar or shaft (more generally a reciprocating member) that is a free sliding fit in a linear bearing, sleeve or bushing. An inside end of the bar or shaft is configured to engage a reciprocating tool. An outside end of the bar or shaft is configured to engage a tool such as a surgical saw blade.

For example, the inside end of the bar or shaft may be shaped like the end of a standard reciprocating saw blade as used by tradespersons and may therefore be engaged by a quick-connect blade coupling of a battery-powered reciprocating saw inside the cover. The outer end of the bar or shaft may have a coupling configured to clamp surgical reciprocating saw blades. The bar or shaft may have stops that limit its travel relative to the baseplate. The combination of a commonly-available battery powered reciprocating saw with a cover according to such an alternative embodiment may be used in place of a much more expensive surgical saw.

Figure 6:
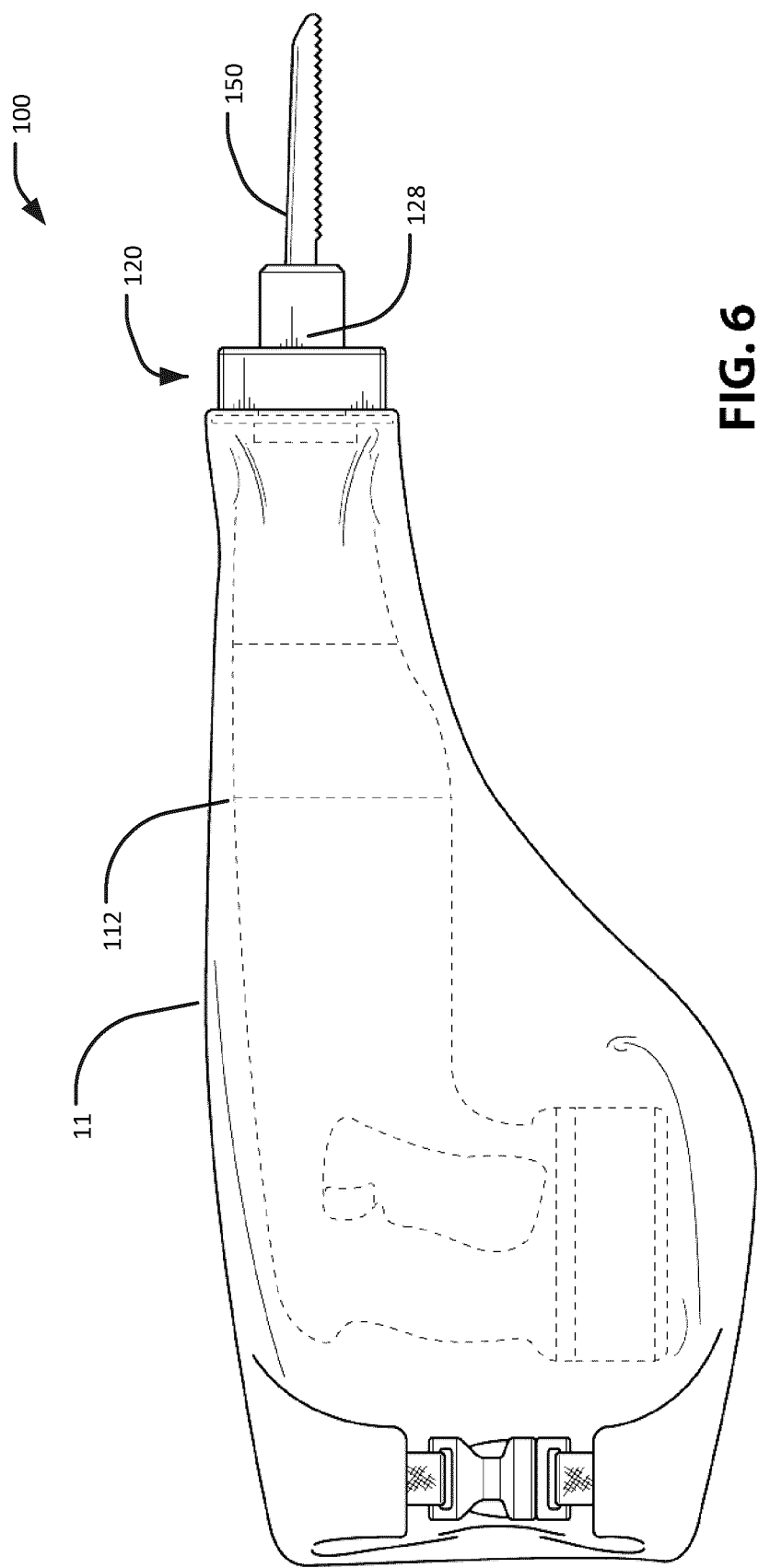
FIG. 6 is a side elevation view of a cover enclosing a reciprocating tool such as a battery-powered reciprocating saw according to an alternative embodiment.

FIG. 6 shows a cover 100 according to an example embodiment that encloses a reciprocating saw 112. Cover 100 includes a bag 11 as described above except that is shaped to accommodate reciprocating saw 112. A reciprocating pass through 120 is sealed to bag 11. Reciprocating pass through 120 may have the same general structure as rotary pass-through 20 which is described above except that it includes a bearing 128 (which may be a linear bearing, sleeve, bushing or the like) that passes reciprocal motion instead of or in addition to the rotary motion which is permitted by bearing 28 in the embodiments described above. A tool 150 outside of cover 100 is reciprocated by tool 112 from inside of cover 100.

A cover 10 as described herein, in combination with a suitable tool 12 may be applied for a wide range of surgical applications including:
- drilling;
- driving a rotary surgical saw;
- surgical reaming;
- wire placement;
- sawing;
- etc.

For each application a power tool 12 may be selected that has appropriate speed and torque characteristics and chuck 21 may be replaced, if necessary with a coupling suitable for the surgical tool to be driven.

Certain embodiments provide one or more of the following advantages:
- rotational movement of a drill is transferred from the inside to the outside of the bag without breaking the sterile seal
- easy to assemble and use in surgery
- allow surgeons to conduct safe and effective surgery with easily sourced and maintained equipment.
- prevents contamination of a tool during surgery,

INTERPRETATION OF TERMS

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a component (e.g. a chuck, member, clamp, closure, tool, bit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A cover for a rotary tool, the cover comprising:
   a flexible enclosure having an inside and an outside;
   a rotary pass through sealed to the flexible enclosure, the rotary pass through comprising a first part that is sealed to the flexible enclosure and supports a bearing seat, a bearing supported by the bearing seat, an inside rotatable member on the inside of the enclosure coupled to rotate an outside rotatable member on the outside of the enclosure, the inside rotatable member configured to engage the rotary tool inside the flexible enclosure, the outside rotatable member configured to engage a tool, the inside rotatable member and the outside rotatable member supported for rotation by the bearing; and
   the flexible enclosure having an opening dimensioned to allow the rotary tool to be put into or removed from the enclosure and a closure arranged to close the opening;
   wherein the bearing seat is provided by a second part that is releasably coupled to the first part by a coupling; and
   wherein the coupling comprises a threaded coupling.

2. A cover according to claim 1 comprising a sealing member that is compressed when the coupling is made up.

3. A cover according to claim 2 wherein the sealing member comprises an O-ring.

4. A cover according to claim 1 supplied in a package having a sterile interior.

5. A cover according to claim 1 in combination with the rotary tool wherein the rotary tool comprises a battery-powered hand drill or power screwdriver.

6. A cover for a rotary tool, the cover comprising:
a flexible enclosure having an inside and an outside;
a rotary pass through sealed to the flexible enclosure, the rotary pass through comprising a first part that is sealed to the flexible enclosure and supports a bearing seat, a bearing supported by the bearing seat, an inside rotatable member on the inside of the enclosure coupled to rotate an outside rotatable member on the outside of the enclosure, the inside rotatable member configured to engage the rotary tool inside the flexible enclosure, the outside rotatable member configured to engage a tool, the inside rotatable member and the outside rotatable member supported for rotation by the bearing; and
the flexible enclosure having an opening dimensioned to allow the rotary tool to be put into or removed from the enclosure and a closure arranged to close the opening;
wherein the bearing seat is provided by a second part that is releasably coupled to the first part by a coupling; and
wherein the rotary pass through extends through a hole in the flexible enclosure, the first part comprises a base plate and a clamping member and an edge of the flexible enclosure surrounding the hole is gripped between the base plate and the clamping member.

7. A cover according to claim 6 wherein the inside rotatable member and the outside rotatable member are provided by opposing ends of a shaft that passes through the bearing.

8. A cover according to claim 7 wherein an outer end of the shaft is hollow.

9. A cover according to claim 8 wherein an outer end of the shaft is larger in diameter than an inner end of the shaft.

10. A cover according to claim 8 wherein at least an inner end of the shaft is solid.

11. A cover according to claim 7 wherein the shaft comprises a longitudinal bore extending through the length of the shaft.

12. A cover according to claim 7 wherein the shaft is one of a plurality of interchangeable shafts, and the plurality of interchangeable shafts include a first shaft having a longitudinal bore in an outer end thereof and a second shaft shorter than the first shaft.

13. A cover according to claim 7 wherein the bearing comprises a roller bearing or a ball bearing which permits free rotation of the shaft relative to the bearing carrier.

14. A cover according to claim 6 wherein the rotary pass through comprises a threaded collar attached to the first part and the inside and outside rotatable members are supported on a threaded member that engages threads of the threaded collar.

15. A cover according to claim 14 wherein the threaded collar has internal threads and the threaded member has external threads.

16. A cover according to claim 6 wherein the inside rotatable member comprises a male hexagonal end formed with a circumferential groove for detachably engaging a quick release hex chuck system of the rotary tool.

17. A cover according to claim 6 wherein the flexible enclosure comprises a fabric bag.

18. A cover according to claim 17 wherein the fabric bag is shaped to conform generally to a shape of the rotary tool.

19. A cover according to claim 18 wherein the rotary tool has an overall L-shaped configuration with a handle extending radially relative to a body and a rotary driven shaft at an end of the body, the flexible enclosure has an overall L-shape and the rotary pass through is at an end of one arm of the L-shape.

20. A cover according to claim 19 wherein seams in the cover are sealed with a tape.

21. A cover according to claim 17 wherein the bag comprises a plurality of layers of fabric including at least an inner layer and an outer layer.

22. A cover according to claim 6 wherein the flexible enclosure is made of a material or materials that will withstand autoclave sterilization at temperatures of at least 120 C.

23. A cover according to claim 6 wherein the outside rotatable member comprises a chuck configured to clampingly engage a tool bit.

24. A cover according to claim 23 wherein the outside rotatable member comprises a three-jaw chuck.

25. A cover according to claim 6 wherein the outside rotatable member comprises a wire gripper comprising a manually-rotatable cam having a first position in which a wire is free to move between the cam and a surface and a second position wherein the cam compresses the wire against the surface, thereby restraining longitudinal movement of the wire.

26. A cover according to claim 6 wherein the flexible enclosure has at least some transparent portions.

27. A cover according to claim 6 wherein the closure comprises a fastener having first and second parts that are detachably affixable to one another, the first and second parts spaced from the opening such that material of the flexible enclosure adjacent the opening may be folded over and the first and second parts may then be affixed together to close the opening.

28. A cover according to claim 6 supplied in a package having a sterile interior.

29. A cover according to claim 6 in combination with the rotary tool wherein the rotary tool comprises a battery-powered hand drill or power screwdriver.

* * * * *